United States Patent [19]

White et al.

[11] 4,075,124

[45] Feb. 21, 1978

[54] PROCESS FOR THE PREPARATION OF UNSATURATED ACIDS FROM UNSATURATED ALDEHYDES

[75] Inventors: James F. White, Akron; Wilfrid G. Shaw, Lyndhurst; Michael D. Applequist, Mayfield Heights, all of Ohio

[73] Assignee: The Standard Oil Company, Cleveland, Ohio

[21] Appl. No.: 733,738

[22] Filed: Oct. 19, 1976

[51] Int. Cl.$^2$ .................. B01J 27/14; C07C 51/24
[52] U.S. Cl. .................. 252/437; 252/435; 260/530 N
[58] Field of Search .................. 252/435; 252/437

[56] References Cited

U.S. PATENT DOCUMENTS

| | | | |
|---|---|---|---|
| 3,684,741 | 8/1972 | Friedrichsen et al. | 252/437 X |
| 3,686,294 | 8/1972 | Ito et al. | 252/437 X |
| 3,761,516 | 9/1973 | Kloobiar | 260/530 N |
| 3,875,220 | 4/1975 | White et al. | 252/437 X |

FOREIGN PATENT DOCUMENTS 2,048,620  4/1971  Germany.

*Primary Examiner*—Patrick P. Garvin
*Assistant Examiner*—William G. Wright
*Attorney, Agent, or Firm*—Gwenetta Douglas Hill; Herbert D. Knudsen; Larry W. Evans

[57] ABSTRACT

Methacrylic acid or acrylic acid are produced by the oxidation of methacrolein or acrolein, respectively, with molecular oxygen in the vapor phase in the presence of a catalytic oxide of molybdenum, phosphorus, arsenic, at least one element selected from the group consisting of Ag, Rh, Ru, and Au, oxygen, and optionally, at least one of Cd, Pt, Tl, Pd, Al, Ge, Cu, Ni, alkaline earth metal, $NH_4$ and Cl.

14 Claims, No Drawings

PROCESS FOR THE PREPARATION OF UNSATURATED ACIDS FROM UNSATURATED ALDEHYDES

BACKGROUND OF THE INVENTION

A number of catalysts are known to be effective for the oxidation of acrolein or methacrolein to acrylic acid or methacrylic acid, respectively. However, the yields obtained using the catalysts for the preparation of methacrylic acid are low. West German Provisional Patent No. 2,048,620 discloses catalysts containing the oxides of molybdenum, phosphorus, and arsenic for the oxidation of methacrolein and acrolein to methacrylic acid and acrylic acid, respectively. U.S. Pat. No. 3,761,516 discloses catalysts containing oxides of molybdenum, arsenic and phosphorus on a support, especially $Al_2O_3$, having external macropores and a surface not greater than 2 m²/g.

The present invention is a result of a search for more efficient and desirable catalysts for the production of acrylic acid and methacrylic acid. Unexpectedly higher yields of and selectivities to acrylic acid and methacrylic acid are obtained by the vapor phase oxidation of acrolein and methacrolein, respectively, with molecular oxygen in the presence of the new and useful catalysts of the present invention.

SUMMARY OF THE INVENTION

It has been discovered according to the present invention in the process for the preparation of acrylic acid or methacrylic acid by the oxidation of acrolein or methacrolein, respectively, with molecular oxygen in the vapor phase at a reaction temperature of about 200° to about 500° C in the presence of an oxide catalyst, and optionally in the presence of steam, the improvement comprising using as a catalyst of the formula $$X_a Y_b Mo_{12} P_c As_d O_x$$

wherein
X is at least one element selected from the group consisting of Ag, Rh, Ru and Au;
Y is at least one of Cd, Tl, Pd, Al, Ge, Cu, Pt, Ni, alkaline earth metal, $NH_4$, and Cl;
and wherein
$a$ is 0.001 to 10;
$b$ is 0 to 10;
$c$ is 0.01 to 5;
$d$ is 0.01 to 5;
$x$ is the number of oxygens required to satisfy the valence states of the other elements present.

The surprisingly advantageous catalysts of this invention give improved yields of acrylic acid and methacrylic acid from acrolein and methacrolein, respectively, in an efficient, convenient, and economical manner at a relatively low temperature. The exotherm of the reaction is low, thereby allowing easy reaction control.

The most significant aspect of the present invention is the catalyst employed. The catalyst may be any of the catalysts delineated by the above formula. The catalysts can be prepared by a number of different techniques described in the art, such as coprecipitation of soluble salts and calcination of the resulting product.

The catalysts of the invention have preferred limitations on their composition. Preferred are catalysts wherein $a$ is 0.001 to 3, catalysts wherein $b$ is 0.001 to 3, and catalysts wherein $b$ is zero.

Especially preferred are catalysts wherein each of the elements described by X is separately incorporated into the catalyst. This is conveniently accomplished by setting X independently equal to the various elements. Also preferred are catalysts wherein Y is at least one of Cd, Tl, Cu, $NH_4$ and Cl.

In the catalyst preparations, the various elements of the catalyst are combined, and the final product is calcined to obtain the catalyst. A number of methods of combining the elements of the catalyst and calcining the resultant product are known to those of skill in the art. In the broad concept of the invention, the particular method of preparing the catalysts is not critical.

There are, however, methods of preparing the catalysts that have been found to be preferred. One preferred preparation involves the preparation of the catalysts in an aqueous slurry or solution of molybdenum, phosphorus and/or arsenic containing components, and adding the remaining components; evaporation of this aqueous mixture; and calcination of the resulting catalysts. Suitable molybdenum compounds that may be employed in the preparation of the catalysts delineated by the above formula include molybdenum trioxide, phosphomolybdic acid, molybdic acid, ammonium heptamolybdate and the like. Suitable phosphorus compounds that may be employed in the preparation of the catalysts include ortho-phosphoric acid, metaphosphoric acid, triphosphoric acid, and phosphorus halides or oxyhalides. The remaining components of the catalysts may be added as oxide, acetate, formate, sulfate, nitrate, carbonate, oxyhalide, or halide and the like.

Excellent results are obtained by refluxing phosphoric acid, an arsenic containing compound, and molybdenum trioxide, or ammonium heptamolybdate in water for about ½ hour to 3 hours, however, commercial phosphomolybdic acid may be effectively utilized; adding the remaining components to the aqueous slurry and boiling to a thick paste; drying at 110° C to 120° C in air; and calcining the resulting catalysts.

The calcination of the catalyst usually is accomplished by heating the dry catalytic components at a temperature of about 200° C to about 700° C. The preferred procedure of the invention is wherein the catalyst is calcined at a temperature of 325° C to 425° C.

The reactants of the reaction of the invention are methacrolein or acrolein and oxygen. Molecular oxygen is normally supplied to the reaction in the form of air, but oxygen gas could also be employed. About 0.5 to about 4 moles of oxygen are normally added per mole of methacrolein.

The reaction temperature may vary as different catalysts are employed. Normally, temperature of about 200° C to about 500° C are employed with temperature of 250° C to 370° C being preferred.

The catalyst may be used alone or a support could be employed. Suitable supports include silica, alumina, Alundum, silicon carbide, boron phosphate, zirconia and titania. The catalysts are conveniently used in a fixed-bed reactor using tablets, pellets or the like or in a fluid-bed reactor using a catalyst having a particle size of less than about 300 microns. When a fluid-bed reactor is employed, preferred catalysts are in the form of microspheroidal particles. The contact time may be as low as a fraction of a second or as high as 20 seconds or more. The reaction may be conducted at atmospheric, superatmospheric or subatmospheric pressure, with absolute pressures of about 0.5 to about 4 atmospheres being preferred.

Excellent results are obtained using a coated catalyst consisting essentially of an inert support material having a diameter of at least 20 microns and an outer surface and a continuous coating of said active catalyst on said inert support strongly adhering to the outer surface of said support. The special coated catalyst consists of an inner support material having an outside surface and a coating of the active catalytic material on this outside surface. These catalysts can be prepared by a number of different methods.

The support material for the catalyst forms the inner core of the catalyst. This is an essentially inert support and may have substantially any particle size although a diameter of greater than 20 microns is preferred. Especially preferred in the present invention for use in a commercial reactor are those supports which are spherical and which have a diameter of about 0.2 cm. to about 2 cm. Suitable examples of essentially inert support materials include: Alundum, silica, alumina, alumina-silica, silicon carbide, titania and zirconia. Especially preferred among these supports and Alundum, silica, alumina and alumina silica.

The catalysts may contain essentially any proportions of support and catalytically active material. The limits of this relationship are only set by the relative ability of the catalyst and support material to accommodate each other. Preferred catalysts contain about 10 to about 100 percent by weight of catalytically active material based on the weight of the support.

The preparation of these coated catalysts can be accomplished by various techniques. The basic method of preparing these catalysts is by partially wetting the support material with a liquid and then contacting the support material with a powder of the catalytically active material and gently agitating the mixture until the catalyst is formed. The gentle agitation is most conveniently accomplished by placing the partially wet support in a rotating drum or jar and adding the powdered active catalytic material.

Using the catalysts of the invention in the preparation of methacrylic acid or acrylic acid, excellent yields are obtained in a convenient reaction with low amounts of byproducts.

SPECIFIC EMBODIMENTS

Comparative Example A to D and Examples 1 to 13:

Comparison of catalysts containing promoters of invention with base catalyst in the preparation of methacrylic acid.

A 20 cc. fixed-bed reactor was constructed of a 1.3 cm. stainless steel tubing equipped with a full length 0.3 cm. axial thermowell. Catalysts prepared as described below were charged to the reactor and heated to the reaction temperature under a flow of air and a feed of methacrolein/air/nitrogen/steam of 1/5.7/4.6/8.7 was fed over the catalyst at an apparent contact time of 2 to 4 seconds. The reactor was run under the reaction conditions for 1 to 6 hours and the product was collected and analyzed.

Comparative Example A and Examples 1 to 6

The catalyts were prepared as follows:

Comparative Example A

25% $Mo_{12}P_1As_{0.5}O_x$ + 75% Alundum

A solution was prepared consisting of 211.88 grams of ammonium heptamolybdate, $(NH_4)_6Mo_7O_{24}\cdot 4H_2O$, (1.2 mole Mo), 500 mls. distilled water at 60° C and 7.94 grams of ammonium arsenate, $NH_4H_2AsO_4$, (0.05 mole As), as solution in 25 mls. distilled water. A white precipitate formed which was heated to about 100° C for 2 hours. To this mixture was added 11.53 grams of 85% solution phosphoric acid (0.10 mole P). One-half hour later 5.0 grams of hydrazine was added. The slurry was evaporated to a thick paste, dried overnight in an oven at 110° to 120° C, and ground and screened to less than 80 mesh. This powder was coated on ⅛ inch SA 5223 Alundum balls by taking 50 grams of Alundum, partially wetting the Alundum with 1.8 grams of water and adding 16.7 grams of active catalyst prepared above in five equal portions. During and after each addition, the Alundum was rolled in a glass jar. The powder was evenly coated onto the surface of the Alundum and the final product was dried. The hard uniform coated catalyst was obtained that consisted of the Alundum support with the continuous, strongly adhering coat of the active catalyst. This material was then calcined for 1 hour at 370° C in 40 ml./min. air to form the active catalyst.

Example 1

25% $Ag_{0.25}Mo_{12}P_1As_{0.5}O_x$ + 75% Alundum

A solution was prepared consisting of 105.9 grams of ammonium heptamolybdate, $(NH_4)_6Mo_7O_{24}\cdot 4H_2O$, (0.6 mole Mo), 700 mls. of distilled water at 60° C and 4.0 grams of ammonium arsenate, $NH_4H_2AsO_4$, (0.025 mole As), as solution in 25 mls. of water. A white precipitate formed which was heated at 100° C about one-half hour. To this mixture was added 2.08 grams of silver acetate (0.0125 mole Ag), followed by the addition of 5.8 grams of 85% solution phosphoric acid (0.05 mole P). One-half hour later 2.5 grams of hydrazine hydrate were added. The slurry was evaporated to a thick paste, dried overnight in an oven at 110° to 120° C, and ground and screened to less than 80 mesh size. The catalyst was then coated to 25% active level on 1/8 inch SA 5223 Alundum balls. Calcination was the same as in Comparative Example A.

Example 2

25% $Au_{0.05}Cd_{0.2}Mo_{12}P_{1.0}As_{0.5}O_x$ + 75% Alundum

This catalyst was prepared in the same manner described in Example 1, except that 150 mls. of water, 34.25 grams of ammonium molybdate, 1.28 grams of ammonium arsenate, 0.862 grams of cadmium acetate, 0.318 grams of gold chloride, 1.86 grams of 85% phosphoric acid and 0.8 grams of hydrazine hydrate were employed.

Example 3

25% $Ru_{0.2}Mo_{12}P_1As_{0.5}O_x$ + 75% Alundum

This catalyst was prepared in the same manner described in Example 1, except that 500 mls. of water, 70.6 grams of ammonium molybdate, 2.64 grams of ammonium arsenate, 1.74 grams of ruthenium chloride, $RuCl_3\cdot 3H_2O$ (0.006 mole Ru), 3.84 grams of phosphoric acid, and 1.6 grams of hydrazine hydrate were employed.

Examples 4 to 6

Preparation of the Catalysts 25% $X_aY_bMo_{12}P_1As_{0.5}O_x$ + 75% Alundum

Various catalysts of the invention were prepared. The catalysts were prepared according to the procedure of Example 1, using 105.9 grams of ammonium molybdate, 700 mls. of 60° C distilled water and 4.0 grams of ammonium arsenate in solution of 25 mls. of water. The catalytic components delineated by X and/or Y were added immediately preceding the addition of 5.8 grams of 85% solution phosphoric acid, and 2.5 grams of hydrazine hydrate. To prepare the catalysts, the following compounds and amounts were used:

| Example | Element | Compound | Amount, g. |
|---|---|---|---|
| 4 | $Ag_{0.1}$ | silver acetate | 0.8 |
| 5 | $Rh_{0.25}$ | rhodium acetate | 2.15 |
| 6 | $Au_{0.25}$ | gold chloride | 4.92 |

Comparative Examples B to D and Examples 7 to 13

The results of the experiments in the oxidation of methacrolein to produce methacrylic acid are shown in the TABLE below. The following definitions are used in measuring the carbon atoms in the feed and the products.

% Single pass yield = $\frac{\text{Moles of Methacrylic Acid Recovered}}{\text{Moles of Methacrolein in the Feed}} \times 100$ Total Conversion = $\frac{\text{Moles of Methacrolein Reacted}}{\text{Moles of Methacrolein in the Feed}} \times 100$ Selectivity = $\frac{\text{Single Pass Yield}}{\text{Total Conversion}} \times 100$ In the same manner described above, catalysts of the invention may be effectively utilized in the preparation of acrylic acid from acrolein.

We claim:

1. The catalyst composition described by the formula $$X_aX_bMo_{12}P_cAs_dO_x$$

wherein
   X is at least one element selected from the group consisting of Ag, Rh, Au and Ru;
   Y is at least one of Cd, Tl, Pd, Al, Ge, Cu, Pt, Ni, alkaline earth metal, $NH_4$ and Cl;
and wherein
   $a$ is 0.001 to 10;
   $b$ is 0 to 10;
   $c$ is 0.01 to 5;
   $d$ is 0.01 to 5;
   $x$ is the number of oxygens required to satisfy the valence states of the other elements present.

2. The catalyst of claim 1 wherein $a$ is 0.001 to 3.
3. The catalyst of claim 1 wherein $b$ is 0.001 to 3.
4. The catalyst of claim 1 wherein $b$ is zero.
5. The catalyst of claim 1 wherein X is silver.
6. The catalyst of claim 1 wherein X is rhodium.
7. The catalyst of claim 1 wherein X is ruthenium.
8. The catalyst of claim 1 wherein X is gold.
9. The catalyst of claim 1 wherein Y is cadmium.
10. The catalyst of claim 1 which is coated on an inert support.
11. The catalyst of claim 10 consisting essentially of an inert support material having a diameter of at least 20 microns and an outer surface and a continuous coating of said active catalyst strongly adhering to the other surface of said support.
12. The catalyst of claim 11 wherein the active catalyst is about 10 to about 100 percent by weight of the inert support.
13. The catalyst of claim 11 wherein the support is selected from the group consisting of silica, alumina, Alundum, aluminasilica, silicon carbide, titania and zirconia.
14. The catalyst of claim 11 wherein the particle size of the inert support is 0.2 cm. to 2 cm.

TABLE

Performance of Catalysts Using the Base Catalyst Compared with Catalysts of the Invention in the Production of Methacrylic Acid

| Example | Catalyst | Reaction Temp. °C | Methacrylic Acid | Acetic Acid | Total Conversion | Selectivity |
|---|---|---|---|---|---|---|
| B | 25%$Mo_{12}P_1As_{0.5}O_x$ + 75% Alundum | 326 | 19.6 | 0.5 | 26.0 | 75.0 |
| C | 25%$Mo_{12}P_1As_{0.5}O_x$ + 75% Alundum | 350 | 43.0 | 1.9 | 56.0 | 76.0 |
| D | 25%$Mo_{12}P_1As_{0.5}O_x$ + 75% Alundum | 376 | 57.0 | 4.8 | 83.0 | 68.0 |
| 7 | 25%$Ag_{.25}Mo_{12}P_1As_{0.5}O_x$ + 75% Alundum | 343 | 60.0 | 3.4 | 74.0 | 81.0 |
| 8 | 25%$Ag_{.1}Mo_{12}P_1As_{0.5}O_x$ + 75% Alundum | 350 | 58.7 | 4.9 | 77.0 | 76.0 |
| 9 | 25%$Rh_{.25}Mo_{12}P_1As_{0.5}O_x$ + 75% Alundum | 350 | 60.0 | 4.8 | 82.0 | 73.0 |
| 10 | 25%$Au_{0.05}Cd_{0.2}Mo_{12}P_1As_{0.5}O_x$ + 75% Alundum | 352 | 62.2 | 4.4 | 85.0 | 73.2 |
| 11 | 25%$Ru_{0.2}Mo_{12}P_1As_{0.5}O_x$ + 75% Alundum | 350 | 51.0 | 5.1 | 75.5 | 68.0 |
| 12 | 25%$Au_{0.25}Mo_{12}P_1As_{0.5}O_x$ + 75% Alundum | 356 | 60.7 | 2.9 | 74.2 | 81.8 |
| 13 | 25%$Au_{0.25}Mo_{12}P_1As_{0.5}O_x$ + 75% Alundum | 364 | 63.5 | 3.5 | 79.4 | 80.0 |

* * * * *

UNITED STATES PATENT AND TRADEMARK OFFICE
CERTIFICATE OF CORRECTION

PATENT NO. : 4,075,124
DATED : February 21, 1978
INVENTOR(S) : James F. White et al It is certified that error appears in the above-identified patent and that said Letters Patent are hereby corrected as shown below:

Column 1: Line 38, after "catalyst" -- a catalyst -- should be inserted.

Line 39 "$X_a X_b Mo_{12} P_c As_d O_x$" should be

-- $X_a Y_b Mo_{12} P_c As_d O_x$ --

Column 3: Line 24 "and" should be --are--

Line 68 "catalyts" should be --catalysts--

In the Claims:

Column 6, Claim 1, Line 2, "$X_a X_b Mo_{12} P_c As_d O_x$" should be

-- $X_a Y_b Mo_{12} P_c As_d O_x$ --.

Signed and Sealed this

*Fifteenth* Day of *August 1978*

[SEAL]

*Attest:*

RUTH C. MASON
*Attesting Officer*

DONALD W. BANNER
*Commissioner of Patents and Trademarks*